US00PP13070P2

(12) United States Plant Patent
van den Aardwegh

(10) Patent No.: US PP13,070 P2
(45) Date of Patent: Oct. 8, 2002

(54) VERONICA PLANT NAMED 'DARWIN'S BLUE'

(75) Inventor: Cornelis Marinus van den Aardwegh, Hillegom (NL)

(73) Assignee: Witteman & Co. 'Multiflora' B.V., Hilliegom (NL)

( * ) Notice: Subject to any disclaimer, the term of this patent is extended or adjusted under 35 U.S.C. 154(b) by 0 days.

(21) Appl. No.: 09/840,803

(22) Filed: Apr. 25, 2001

(51) Int. Cl.[7] ..... A01H 5/00
(52) U.S. Cl. ..... Plt./251
(58) Field of Search ..... Plt./251

(56) References Cited

PUBLICATIONS

UPOV ROM GTITM Computer Database, GTI JOUVE Retrieval Software 202/02, citation for 'Darwin's Blue'.*

* cited by examiner

*Primary Examiner*—Bruce R. Campell
*Assistant Examiner*—Wendy Couchoud Baker
(74) *Attorney, Agent, or Firm*—C. A. Whealy

(57) ABSTRACT

A new and distinct cultivar of Veronica plant named 'Darwin's Blue', characterized by its upright plant habit; freely flowering habit; and dark violet blue-colored flowers.

2 Drawing Sheets

BOTANICAL CLASSIFICATION

*Veronica spicata.*

BACKGROUND OF THE INVENTION

The present Invention relates to a new and distinct cultivar of Veronica plant, botanically known as *Veronica spicata*, and hereinafter referred to by the name 'Darwin's Blue'.

The new Veronica is a naturally-occurring whole plant mutation of an unidentified selection of *Veronica spicata*, not patented. The new Veronica was discovered by the Inventor in a controlled environment in Hillegom, The Netherlands, within a population of plants of the unidentified selection in 1998. The selection of this new Veronica was based on its dark violet blue flower color. Plants of the new Veronica have darker violet blue-colored flowers than plants of the parent selection.

Asexual reproduction of the new cultivar by vegetative cuttings taken at Hillegom, The Netherlands since 1999, has shown that the unique features of this new Veronica are stable and reproduced true to type in successive generations.

SUMMARY OF THE INVENTION

Plants of the cultivar Darwin's Blue have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Darwin's Blue'. These characteristics in combination distinguish 'Darwin's Blue' as a new and distinct cultivar:

1. Upright plant habit.
2. Freely flowering habit.
3. Dark violet blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Veronica.

The photograph at the top of the first sheet comprises a side perspective view of a typical flowering plant of 'Darwin's Blue'.

The photograph at the top of the second sheet comprises a close-up view of typical inflorescences of 'Darwin's Blue'.

The photograph at the bottom of the second sheet comprises a close-up view of the upper surface of mature and young leaves of 'Darwin's Blue'.

DETAILED BOTANICAL DESCRIPTION

The following observations, measurements and values describe plants of the new cultivar grown in the field under outdoor conditions during the summer in Hillegom, The Netherlands. Plants used in the photographs and the detailed botanical description were about 25 weeks from planting rooted cuttings. Color references are made to The Royal Horticultural Society Colour Chart except where general terms of ordinary dictionary significance are used.

Botanical classification: *Veronica spicata* cultivar Darwin's Blue.

Parentage: Naturally-occurring whole plant mutation of an unidentified selection of *Veronica spicata*, not patented.

Propagation:

*Type cutting.*—Vegetative cuttings.

*Time to produce a rooted liner.*—About 30 days during the spring in Hillegom, The Netherlands.

*Root description.*—Fine, fibrous.

Plant description:

*Form.*—Upright, broad inverted triangle.

*Usage.*—Perennial garden plant.

*Crop time.*—From cuttings, about 25 weeks are required to produce fully-grown flowering plants in 1.5-liter containers.

*Plant height.*—About 40 cm.

*Area of spread.*—About 50 cm.

*Vigor.*—Moderately vigorous.

*Branching habit.*—Very freely branching; about 14 lateral branches develop per plant.

*Lateral branches.*—Length: About 30 cm. Diameter: About 2 mm. Internode length: About 5 cm. Texture: Pubescent. Color: 143A to 143C.

*Foliage description.*—Leaves simple, opposite, generally symmetrical, durable and long persisting. Length: About 7 cm. Width: About 2.2 cm. Shape: Narrowly ovate to lanceolate. Apex: Acuminate. Base: Attenuate. Margin: Serrulate. Texture: Upper surface: Glabrous. Lower surface: Pubescent. Venation pattern: Pinnate. Color: Young foliage, upper surface: 141A. Young foliage, lower surface: 138A. Mature foliage, upper surface: 137A. Mature foliage, lower surface: 137C. Venation, upper surface: 137A. Venation, lower surface: 143C. Petiole: Length: About 5 mm. Diameter: About 1 by 2 mm. Texture, both surfaces: Smooth. Color: Upper surface 137A. Lower surface: 137C.

Flower description:

*Flower type and habit.*—Single campanulate dark violet blue-colored flowers arranged in upright racemes; flowers face mostly outward. Flowers not persistent.

*Natural flowering season.*—Flowering continuous during the summer from early July to mid-September in Hillegom, The Netherlands.

*Quantity of flowers.*—Freely flowering with one to five flowering racemes per lateral branch and more than 140 open flowers and flower buds per flowering raceme.

*Fragrance.*—Not detected.

*Flower longevity on the plant.*—About 6 to 8 days.

*Flower longevity as a cut flower.*—More than 14 days.

*Flower buds.*—Length: About 4 cm. Diameter: About 1.75 cm. Shape: Elliptic. Color: 93C to 93D.

*Corolla.*—Arrangement: Four-parted, petals fused at base, cupped or campanulate. Flower diameter: About 6 mm. Flower height (depth): About 8 mm. Petal length: About 5 mm. Petal width: About 4 mm. Petal shape: Obovate. Petal apex: Obtuse. Petal margin: Entire. Texture: Smooth, sparsely covered with very short, less than 0.1 mm, pale grayish hairs at the base. Petal color: When opening, upper and lower surfaces: 93B. Opened flower, upper surface: 93A to 93B. Opened flower, lower surface: 93B.

*Calyx.*—Calyx length: About 3 mm. Calyx diameter: About 2 mm. Sepal arrangement: Four fused at base, campanulate. Sepal shape: Lanceolate. Sepal apex: Acute. Sepal margin: Entire. Sepal texture, both surfaces: Smooth. Sepal color, both surfaces: 137A to 137B.

*Peduncle.*—Angle: About 45 to 60° from stem. Strength: Strong. Length: About 1 mm. Diameter: Less than 1 mm. Color: 137A.

*Reproductive organs.*—Stamens: Stamen quantity: Two per flower. Anther shape: Reniform; dorsifixed. Anther length: About 1 mm. Anther color: Towards center, close to 93C, towards margins, close to 155D. Pollen amount: Moderate to abundant. Pollen color: 4C. Pistils: Pistil quantity: One per flower. Pistil length: About 7 mm. Stigma shape: Flattened. Stigma color: 93A. Style length: About 7 mm. Style color: 93A. Ovary color: 143C.

*Seed.*—Length: About 1 mm. Diameter: About 0.5 mm. Color: Dark grayish brown.

Disease/pest resistance: Resistance to pathogens or pests common to Veronica has not been observed.

It is claimed:

1. A new and distinct cultivar of Veronica plant named 'Darwin's Blue', as illustrated and described.

* * * * *

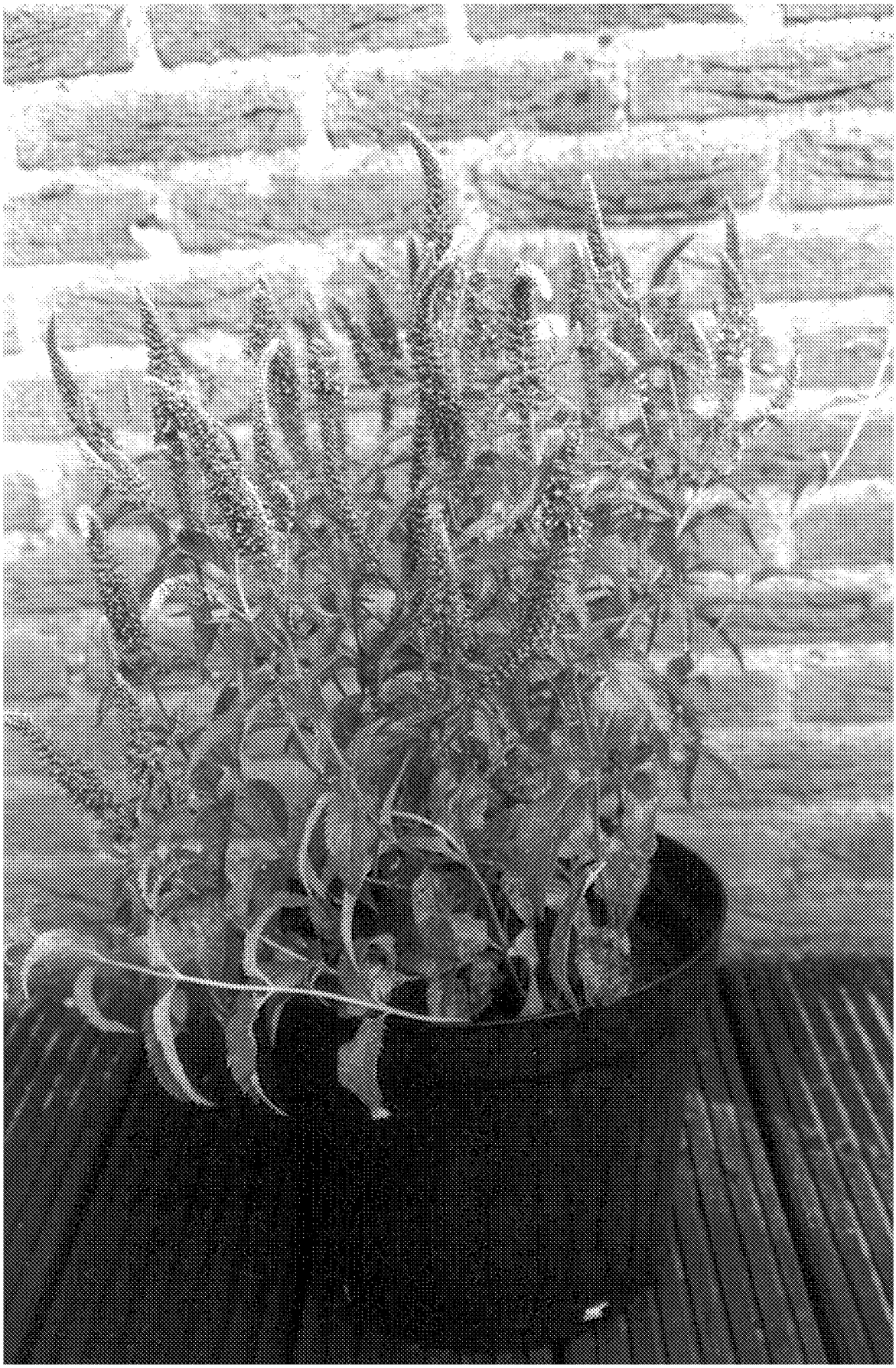

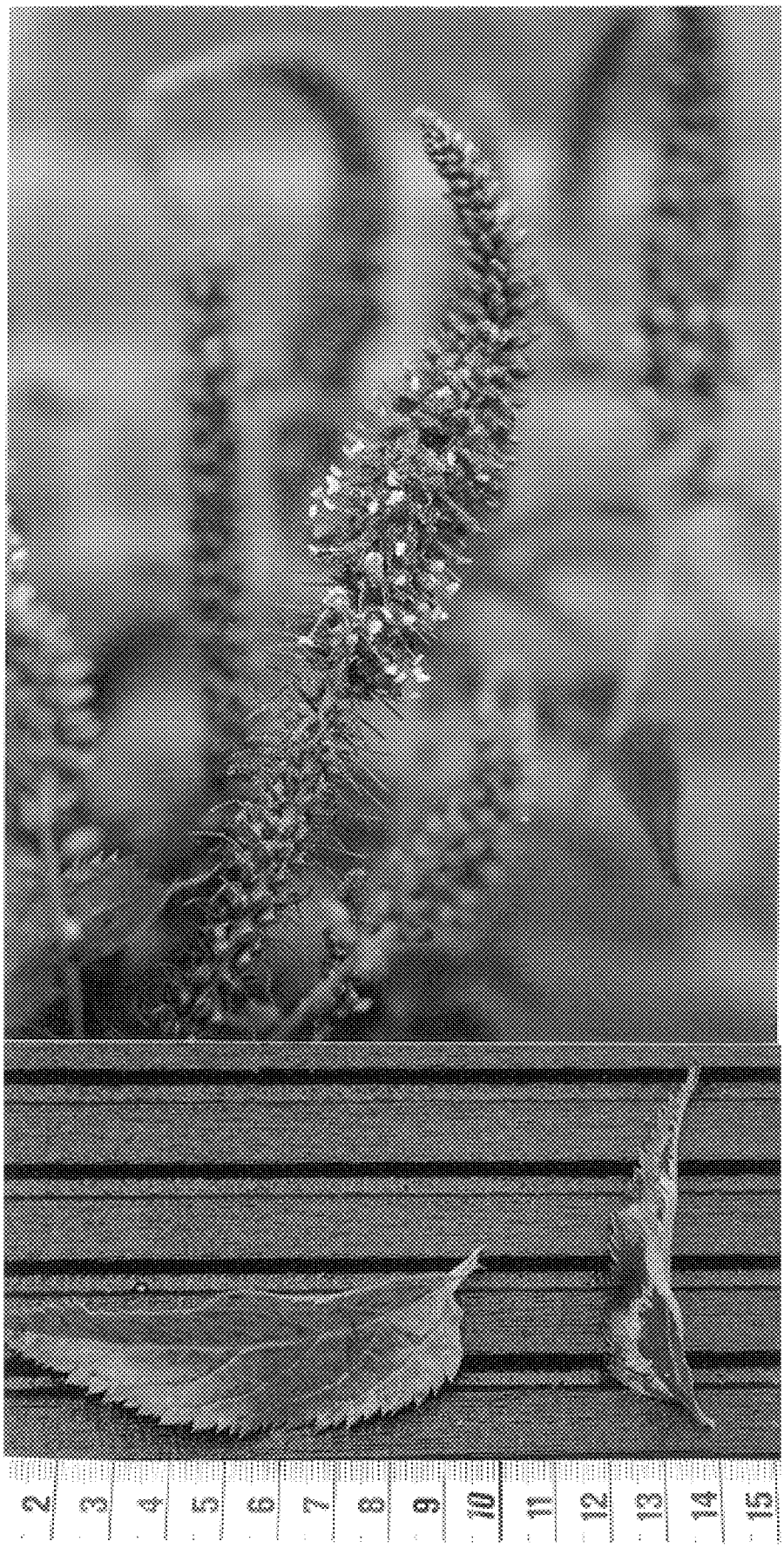
2
3
4
5
6
7
8
9
10
11
12
13
14
15